(12) United States Patent
Bertrand et al.

(10) Patent No.: US 8,017,646 B2
(45) Date of Patent: Sep. 13, 2011

(54) HISTAMINE $H_3$-RECEPTOR LIGANDS AND THEIR THERAPEUTIC APPLICATION

(75) Inventors: Isabelle Bertrand, Pace (FR); Marc Capet, Melesse (FR); Jeanne-Marie Lecomte, Paris (FR); Nicolas Levoin, Mordelles (FR); Xavier Ligneau, Saint Gregoire (FR); Olivia Poupardin-Olivier, Varois et Chaignot (FR); Philippe Robert, Pace (FR); Jean-Charles Schwartz, Paris (FR)

(73) Assignee: Bioprojet, Paris (FR)

( * ) Notice: Subject to any disclaimer, the term of this patent is extended or adjusted under 35 U.S.C. 154(b) by 458 days.

(21) Appl. No.: 11/912,812

(22) PCT Filed: Apr. 26, 2006

(86) PCT No.: PCT/IB2006/001018
§ 371 (c)(1),
(2), (4) Date: Oct. 26, 2007

(87) PCT Pub. No.: WO2006/117611
PCT Pub. Date: Nov. 9, 2006

(65) Prior Publication Data
US 2008/0182876 A1    Jul. 31, 2008

Related U.S. Application Data

(60) Provisional application No. 60/678,242, filed on May 6, 2005.

(30) Foreign Application Priority Data

Apr. 29, 2005 (EP) .................................... 05290948

(51) Int. Cl.
*A61K 31/40* (2006.01)
*C07D 207/08* (2006.01)
(52) U.S. Cl. ...................................... 514/420; 548/574
(58) Field of Classification Search .................. 548/574
See application file for complete search history.

(56) References Cited

U.S. PATENT DOCUMENTS

| | | | |
|---|---|---|---|
| 3,651,067 A | 3/1972 | Elpern et al. | |
| 4,707,487 A | 11/1987 | Arrang et al. | |
| 4,948,796 A | 8/1990 | Hiraiwa et al. | |
| 5,290,790 A | 3/1994 | Arrang et al. | |
| 5,463,074 A | 10/1995 | Shih et al. | |
| 5,486,526 A | 1/1996 | Durant et al. | |
| 5,559,113 A | 9/1996 | Schwartz et al. | |
| 5,578,616 A | 11/1996 | Aslanian et al. | |
| 5,639,775 A | 6/1997 | Durant et al. | |
| 5,663,350 A | 9/1997 | Durant et al. | |
| 5,990,317 A | 11/1999 | Phillips et al. | |
| 6,080,871 A | 6/2000 | Kalindjian et al. | |
| 6,166,060 A | 12/2000 | Phillips et al. | |
| 6,248,765 B1 | 6/2001 | Schwartz et al. | |
| 7,138,413 B1 | 11/2006 | Schwartz et al. | |
| 2005/0113435 A1 | 5/2005 | Hancock et al. | |

FOREIGN PATENT DOCUMENTS

| EP | 0 680 960 | | 11/1995 |
|---|---|---|---|
| WO | WO-92/15567 | | 9/1992 |
| WO | WO-93/12107 | | 6/1993 |
| WO | WO-95/06037 | | 3/1995 |
| WO | WO-95/11894 | | 5/1995 |
| WO | WO-96/40126 | | 12/1996 |
| WO | WO 00/06254 | * | 2/2000 |
| WO | WO-01/74815 | | 10/2001 |
| WO | WO-02/076925 | | 10/2002 |

OTHER PUBLICATIONS

Concise Encyclopedia Chemistry (1993) Walter de Gruyter Berlin New York.*
Vippagunta, et al. Advanced Drug Delivery Reviews, (2001), 48, pp. 3-26.*
Antoniadou-Vyzas et al, "Synthese et etude pharmacologique d'aminoethers ecombres", 1984, pp. 239-242, vol. 42, No. 3, Ann. Pharmaceutiques francaises, Paris.

* cited by examiner

*Primary Examiner* — Shawquia Young
(74) *Attorney, Agent, or Firm* — B. Aaron Schulman, Esq.; Terry L. Wright, Esq.; Stites & Harbison PLLC

(57) ABSTRACT

The present patent application concerns new compounds of formula (I) with $R^1$ and $R^2$ taken together with the nitrogen atom to which they are attached, form a saturated nitrogen-containing ring, A is a saturated C1-4 alkylene and B a C3-4 alkylene or alkenylene chain; their preparation and their use as a H3 receptor ligand for treating e.g. CNS disorders like Alzheimer's disease.

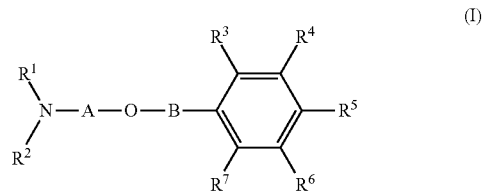

(I)

13 Claims, No Drawings

HISTAMINE H₃-RECEPTOR LIGANDS AND THEIR THERAPEUTIC APPLICATION

CROSS-REFERENCE TO RELATED APPLICATIONS

This Application is a §371 National Stage Application of International Application No. PCT/IB2006/001018, filed Apr. 26, 2006; which claims priority from U.S. Provisional Application No. 60/678,242, filed May 6, 2005, and from European Patent Application 05290948.8, filed Apr. 29, 2005.

The present patent application concerns new ligands of the H₃-receptor, their process of preparation and their therapeutic use.

Antagonists of histamine H₃-receptor are known especially to increase synthesis and release of cerebral histamine. Through this mechanism, they induce an extended wakefulness, an improvement in cognitive processes, a reduction in food intake and a normalization of vestibular reflexes (Schwartz et al., *Physiol. Rev.*, 1991, 71: 1-51).

Histamine H₃-receptor agonists are known to inhibit the release of several neurotransmitters including histamine, monoamines and neuropeptides and thereby exert sedative and sleep-promoting effects in brain. In peripheral tissues, H₃-receptor agonists exert namely anti-inflammatory, anti-nociceptive, gastro-intestinal, antisecretory smooth muscle decontracting activities.

H₃ receptor antagonist or agonist compounds previously known resemble histamine in possessing an imidazole ring generally monosubstituted in 4(5)-position (Ganellin et al., *Ars Pharmaceutica*, 1995, 36:3, 455-468; Stark et al., *Drug of the Future*, 1996, 21(5), 507-520).

Numerous patents and patent applications are directed to antagonist and/or agonist compounds having such structure, in particular EP 197 840, EP 494 010, WO 93/14070, WO 96/29315, WO 92/15 567, WO 93/20061, WO 93/20062, WO 95/11894, U.S. Pat. No. 5 486 526, WO 93/12107, WO 93/12108, WO 95/14007, WO 95/06037, WO 97/29092, EP 680 960, WO 96/38141, WO 96/38142, WO 96/40126.

In the literature, Plazzi et al., *Eur. J. Med. Chem.*, 1995, 30, 881, Clitherow et al., *Bioorg. & Med. Chem. Lett.*, 6 (7), 833-838 (1996), Wolin et al., *Bioorg. & Med. Chem. Lett.*, 8, 2157 (1998) can be cited also in this respect.

Nevertheless, such imidazole derivatives may show drawbacks such as poor blood-brain barrier penetration, interaction with cytochrome P-450 proteins and/or some hepatic and ocular toxicities.

Non-imidazole known neuro-active compounds such as betahistine (J-M. Arrang et al., *Eur. J. Pharmacol.*, 1985,111: 72-84), phencyclidine (J-M. Arrang et al., *Eur. J. Pharmacol.*, 1988,157: 31-35), dimaprit (J.-C. Schwartz et al., *Agents Actions*, 1990, 30: 13-23), clozapine (M. Kathmann et al., *Psychopharmacology* 1994, 116: 464-468), and sesquiterpenes (M. Takigawa et al., JP 06 345 642 (20 Dec. 1994)) were suggested to display H₃-receptor antagonism but all these compounds have only very low potency.

These compounds were previously known as therapeutic agent before the discovery and characterization of the histamine H₃-receptor, in particular as neuro-active agents for example as neuroleptic (clozapine) or psychotomimetic (Phencyclidine) agent.

When tested at the H₃-receptor, these compounds were shown to display much lower potency than the imidazole-containing compounds described in patent applications quoted above.

Contrary to previous attempts, the inventors succeeded at developing potent H₃-receptor ligands not containing imidazole ring that reduced the above-mentioned drawbacks. These compounds, their preparation and therapeutical applications thereof have been described in the international patent application WO 00/06254.

More specifically, WO 00/06254 discloses, inter allia, compounds of formula (IIa):

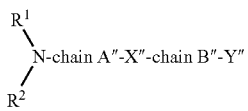

More precisely, formula (IIa) depicts a general pharmacophore that is furthermore widely exemplified in the above-mentioned patent.

For pharmaceutical use, it is desirable to have compounds that are metabolically stable. A general way for metabolising aromatics is the para oxidation. So it is wise to focus on compounds having a substituent in this position or a bulky substituent in the meta position.

However, the inventors have found that compounds of WO 00/06254 exhibiting a para-substituted group generally inhibit cytochromes 2D6 or 3A4. This is particularly deleterious for pharmaceuticals as these cytochromes are both involved in metabolisation of xenobiotics and biotransformation of endogenous products.

Surprisingly, the inventors have now discovered that some specific modifications on these structures both afford compounds displaying a very good affinity for the human H₃ receptor (Ki<7 nM) together with a dramatically reduced inhibition of cytochromes 2D6 and 3A4. This is expressed by a Ki largely over the micromolar and/or a percentage of inhibition clearly under 50% when the compound is assessed at 1 μM.

The present invention is directed to these novel compounds which fulfill these requirements.

Additionally, preferred compounds of the invention exhibit a low HERG activity. Those showing a good bioavailability are particularly preferred.

According to a first object, the present invention concerns new compounds of formula (I):

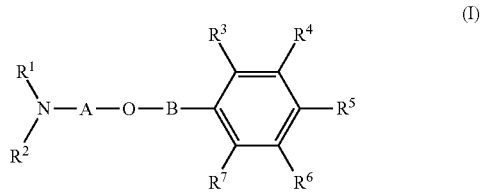

with R¹ and R² taken together with the nitrogen atom to which they are attached, form a saturated nitrogen-containing ring:

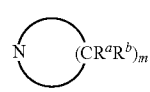

with m ranging from 4 to 6, each $R^a$, $R^b$ is independently identical or different, and $R^a$ represent a hydrogen and $R^b$ represents a hydrogen or a $C_1$-$C_4$ alkyl, or 2 $R^b$ form together a bond so as to form a bicyclic ring, such as, for example

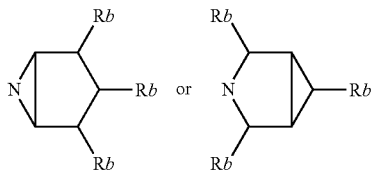

chain A is a saturated linear C1-C4 alkylene, preferably C2-C4 alkylene chain B is chosen from the groups $C_3$-$C_4$ linear alkylene or $C_3$-$C_4$ linear alkenylene and $R^5$ is chosen from a fluor atom, —$C_1$-$C_4$ alkyl, —O($C_1$-$C_4$) Alkyl, —OH, $CF_3$, an unbranched or branched alkenyl, an unbranched or branched alkynyl, -O(aryl), —$CH_2CN$, —(O)$_n$—X—$NR^8R^9$ wherein n=0 or 1, X represents an alkylene, alkenylene, alkynylene, with $R^8$ and $R^9$ representing independently hydrogen, a straight or branched $C_1$-$C_4$ alkyl, an aryl group or taken together with the nitrogen atom to which they are attached form a saturated or partially unsaturated monocyclic or bicyclic heterocycle;

or $R^4$ and $R^5$ form together a cycle or heterocycle, fused with the phenyl group, said cycle or heterocycle being aromatic, saturated, unsaturated or partially unsaturated, each of $R^3$, $R^4$, $R^6$, $R^7$ identical or different independently represents a group chosen from H, —$C_1$-$C_4$ alkyl, halogen atom, —O($C_1$-$C_4$)Alkyl, —OH, $CF_3$, an unbranched or branched alkene, an unbranched or branched alkyne, —O(aryl), —$CH_2CN$, —(O)$_n$—X—$NR^8R^9$ wherein n=0 or 1, X represents an alkylene, alkenylene, alkynylene, with $R^8$ and $R^9$ representing independently hydrogen, a straight or branched $C_1$-$C_4$ alkyl, an aryl group or taken together with the nitrogen atom to which they are attached form a saturated or partially unsaturated monocyclic or bicyclic heterocycle;

or $R^3$ and $R^4$ form together a cycle or heterocycle, fused with the phenyl group, said cycle or heterocycle being aromatic, saturated, unsaturated or partially unsaturated, or their pharmaceutically acceptable salts, hydrates, or hydrated salts, or the polymorphic crystalline structures of these compounds or their optical isomers, racemates, diastereomers or enantiomers.

Preferably, chain B is chosen from the groups selected within $C_3$-$C_4$ linear alkylene;

A is a saturated linear C2-C4 alkylene;

$R^5$ is chosen from a fluor atom, —$C_1$-$C_4$ alkyl, —O($C_1$-$C_4$) Alkyl, —OH;

each of $R^3$, $R^4$, $R^6$, $R^7$ identical or different independently represents a group chosen from H, —$C_1$-$C_4$ alkyl, Halogen atom, —O($C_1$-$C_4$)Alkyl, —OH.

According to a preferred aspect, chain B is chosen from the groups selected within $C_3$-$C_4$ linear alkylene or $C_3$-$C_4$ linear alkenylene;

A is a saturated linear C2-C4 alkylene;

$R^5$ is chosen from a fluor atom, —O($C_1$-$C_4$)Alkyl, and/or each of $R^3$, $R^4$, $R^6$, $R^7$ represents H, or $R^4$ and $R^5$ form together a saturated heterocycle fused with the phenyl group, and each of $R^3$ $R^6$, $R^7$ represents H.

According to a more preferred aspect:

chain B is chosen from the groups selected within $C_3$-$C_4$ linear alkylene or $C_3$-$C_4$ linear alkenylene;

A is a saturated linear C2-C4 alkylene;

$R^5$ is chosen from a fluor atom, and/or each of $R^3$, $R^4$, $R^6$, $R^7$ represents H, or $R^4$ and $R^5$ form together a saturated heterocycle fused with the phenyl group, and each of $R^3$ $R^6$, $R^7$ represents H.

Preferred compounds of formula (I) are chosen from:
1-{3-[3-(3,4-dimethoxyphenyl)propoxy]propyl}pyrrolidine,
trans-1-{3-[3-(3,4-dimethoxyphenyl)allyloxy]propyl}piperidine,
1-{3-[3-(3,4-dimethoxyphenyl)propoxy]propyl}piperidine,
1-{3-[3-(4-methylphenyl)propoxy]propyl}piperidine,
1-{3-[3-(2-naphtyl)propoxy]propyl}piperidine,
1-{3-[3-(4-hydroxy-3-methoxyphenyl)propoxy]propyl}piperidine,
1-{3-[3-(4-fluorophenyl)propoxy]propyl}pyrrolidine,
trans-1-{3-[3-(4-fluoro-3-methoxyphenyl)allyloxy]propyl}pyrrolidine,
1-{3-[3-(4-fluoro-3-methoxyphenyl)propoxy]propyl}pyrrolidine,
1-{3-[3-(4-fluoro-3-methylphenyl)propoxy]propyl}pyrrolidine,
1-{3-[3-(4-fluoro-2-methoxyphenyl)propoxy]propyl}pyrrolidine,
trans-1-{3-[3-(benzofuran-5-yl)allyloxy]propyl}pyrrolidine,
1-{3-[3-(2,3-dihydrobenzo[1,4]dioxin-6-yl)allyl]oxy}propyl)piperidine,
trans-1-{3-[3-(benzodioxol-5-yl)allyloxy]propyl}pyrrolidine, or their pharmaceutically acceptable salts, hydrates, or hydrated salts, or the polymorphic crystalline structures of these compounds or their optical isomers, racemates, diastereomers or enantiomers.

More particularly:
1-{3-[3-(4-fluorophenyl)propoxy]propyl}pyrrolidine,
or their pharmaceutically acceptable salts, hydrates, or hydrated salts, or the polymorphic crystalline structures of these compounds or their optical isomers, racemates, diastereomers or enantiomers.

The following compounds are of specific interest:
1-{3-[3-(3,4-dimethoxyphenyl)propoxy]propyl}pyrrolidine,
1-{3-[3-(3,4-dimethoxyphenyl)propoxy]propyl}piperidine,
1-{3-[3-(4-fluorophenyl)propoxy]propyl}pyrrolidine,
1-{3-[3-(4-fluoro-3-methoxyphenyl)propoxy]propyl}pyrrolidine,
trans-1-{3-[3-(benzodioxol-5-yl)allyloxy]propyl}pyrrolidine, or their pharmaceutically acceptable salts, hydrates, or hydrated salts, or the polymorphic crystalline structures of these compounds or their optical isomers, racemates, diastereomers or enantiomers.

The following compounds are of more specific interest:
1-{3-[3-(4-fluorophenyl)propoxy]propyl}pyrrolidine,
trans-1-{3-[3-(benzodioxol-5-yl)allyloxy]propyl}pyrrolidine,
or their pharmaceutically acceptable salts, hydrates, or hydrated salts, or the polymorphic crystalline structures of these compounds or their optical isomers, racemates, diastereomers or enantiomers.

As used hereabove or hereafter:

"Alkyl" means an aliphatic hydrocarbon group which may be straight or branched having 1 to 20 carbon atoms in the chain. Preferred alkyl groups have 1 to 12, preferably 1 to 4 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Alken" means an aliphatic hydrocarbon group containing a carbon-carbon double bond and which may be straight or branched having 2 to 15 carbon atoms in the chain. Preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkyn" means an aliphatic hydrocarbon group containing a carbon-carbon triple bond and which may be straight or branched having 2 to 15 carbon atoms in the chain. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

"Halogen atom" refers to fluorine, chlorine, bromine or iodine atom; preferably fluorine and chlorine atom.

"Aryl" means an aromatic monocyclic or multicyclic hydrocarbon ring system of 6 to 14 carbon atoms, preferably of 6 to 10 carbon atoms. Exemplary aryl groups include phenyl or naphthyl.

As used herein, the terms "heterocycle" or "heterocyclic" refer to a saturated, partially unsaturated or unsaturated, non aromatic stable 3 to 14, preferably 5 or 6 to 10 membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in The Handbook of Chemistry and Physics, 76$^{th}$ Edition, CRC Press, Inc., 1995-1996, pages 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydropyranyl, dioxanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyridyl, dihydropyridyl, tetrahydropyrinidinyl, dihydrothiopyranyl, azepanyl, as well as the fused systems resulting from the condensation with a phenyl group.

As used herein, the term "heteroaryl" or aromatic heterocycles refers to a 5, 6 to 14, preferably 5, 6 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thiazolyl, benzothiazolyl, furanyl, benzofuranyl, 1,2,4-thiadiazolyl, isothiazolyl, triazoyl, isoquinolyl, benzothienyl, isobenzofuryl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocycle" and the likes refers also to the corresponding "alkylene", "cycloalkylene", "alkenylene", "alkynylene", "arylene", "heteroarylene", "heterocyclene" and the likes which are formed by the removal of two hydrogen atoms.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, compositions, or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfanic, phosphoric, nitric and the like; and the salts prepared from organic acids such as acetic, propionic, succinic, tartaric, citric, methanesulfonic, benzenesulfonic, glucuronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium. Hydrochloride and oxalate salts are preferred.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

The compounds of the general formula (I) having geometrical and stereoisomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

The process of preparation of a compound of formula (I) of the invention is a further object of the present invention.

According to a first aspect, compounds of the invention of formula (I) can be obtained from corresponding compounds of formula (II)

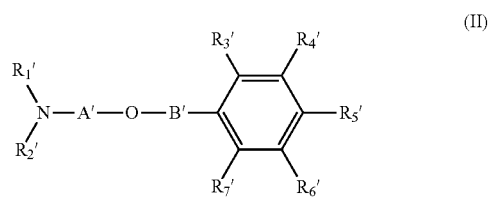

(II)

wherein A', B', $R_1'$, $R_2'$, $R_3'$, $R_4'$, $R_5'$, $R_6'$ and $R_7'$ represent respectively A, B, $R_1$, $R_2$, $R_3$, $R_4$, $R_5$, $R_6$ and $R_7$ or a precursor group of respectively A, B, $R_1$, $R_2$, $R_3$, $R_4$, $R_5$, $R_6$ and $R_7$.

According to the present invention, the expression "precursor group" of a functional group refers to any group which can, by one or more reactions, lead to the desired function, by means of one or more suitable reagents. Those reactions include the de-protecting group, as well as usual addition, substitution or functionalization reactions.

Preferably, a compound of formula (I) in which B represents an alkyl chain can be prepared from a corresponding compound of formula (II) in which B' represents an alkenyl chain, by a hydrogenation reaction. Generally, this reaction is carried out under catalytic conditions by using a catalyst such as Pd/C or platinum oxide. Preferably, this reaction can be carried out by simultaneously deprotecting any protective group of A, B, $R_1$, $R_2$, $R_3$, $R_4$, $R_5$, $R_6$ and $R_7$ which may be present in compound of formula (II).

According to a second aspect, compounds of the invention of formula (I) can be obtained by reacting corresponding compounds of formula (III) and (IV):

(III)

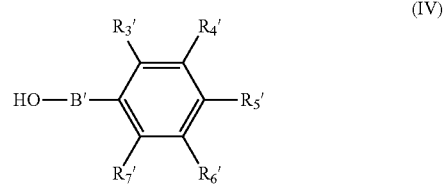

(IV)

in which wherein A', B', $R_1'$, $R_2'$, $R_3'$, $R_4'$, $R_5'$, $R_6'$ and $R_7'$ represent respectively A, B, $R_1$, $R_2$, $R_3$, $R_4$, $R_5$, $R_6$ and $R_7$ or a precursor group of respectively A, B, $R_1$, $R_2$, $R_3$, $R_4$, $R_5$, $R_6$ and $R_7$ and X represents a halogen atom. Generally, this reaction is carried out under basic conditions.

According to a further aspect, compounds of the invention of formula (I) can be obtained by reacting corresponding compounds of formula (V) and (VI):

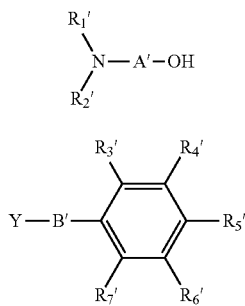

(V)

(VI)

in which wherein A', B', $R_1'$, $R_2'$, $R_3'$, $R_4'$, $R_5'$, $R_6'$ and $R_7'$ represent respectively A, B, $R_1$, $R_2$, $R_3$, $R_4$, $R_5$, $R_6$ and $R_7$ or a precursor group of respectively A, B, $R_1$, $R_2$, $R_3$, $R_4$, $R_5$, $R_6$ and $R_7$ and Y represents a leaving group, such as OMs or halogen for example. Generally, this reaction is carried out under basic conditions.

According to a further aspect, compounds of the invention of formula (I) can be obtained by reacting corresponding compounds of formula (VII) and (VIII):

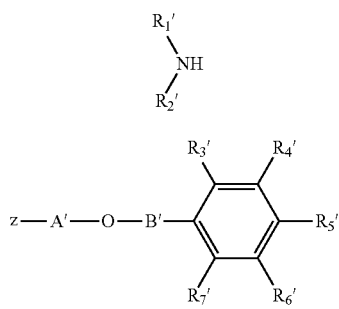

(VII)

(VIII)

in which wherein A', B', $R_1'$, $R_2'$, $R_3'$, $R_4'$, $R_5'$, $R_6'$ and $R_7'$ represent respectively A, B, $R_1$, $R_2$, $R_3$, $R_4$, $R_5$, $R_6$ and $R_7$ or a precursor group of respectively A, B, $R_1$, $R_2$, $R_3$, $R_4$, $R_5$, $R_6$ and $R_7$ and Z represents a halogen atom. Generally, this reaction is carried out under basic conditions.

Further, the process of the invention may also comprise the additional step of isolating the compound of formula (I). This can be done by the skilled person by any of the known conventional means, such as the recovery methods described above.

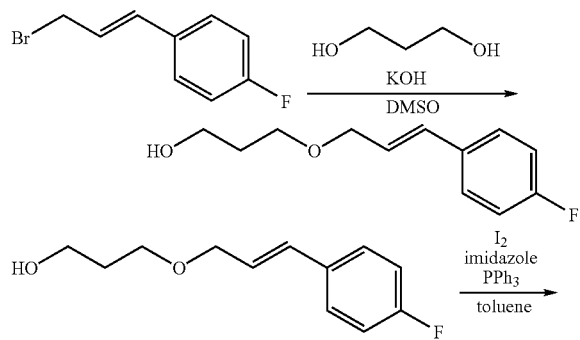

The starting products are commercially available or may be obtained by applying or adapting any known methods or those described in the examples.

The synthesis may also be carried out in one pot as a multicomponent reaction.

According to a further object, the present invention is also concerned with pharmaceutical compositions comprising a compound of formula (I) together with a pharmaceutically acceptable excipient or carrier.

The antagonists are advantageously used as active ingredient in particular, of medicaments having psychotropic effects, promoting wakefulness, attention, memory and improving mood, in treatment of pathologies such as Alzheimer's disease and other cognitive disorders in aged persons, depressive or simply asthenic states. Preferably, said compounds may be used to treat and/or prevent CNS disorders, such as Alzheimer's disease, attention, wakefulness, memorization disorders, cognitive deficits in psychiatric pathologies, in particular in aged persons, depressive or asthenia states.

Their nootropic effects can be useful to stimulate vigilance, attention and memorization capacity in healthy humans. The compounds of the invention can also be useful to facilitate night work or adaptation to time shift in humans.

In addition, these agents can be useful in treatment of obesity, vertigo and motion sickness.

It can also be useful to associate the compounds of the invention with other psychiatric agents such as neuroleptics to increase their efficiency and reduce their side effects.

Application in certain forms of epilepsy is also foreseen.

Their therapeutic applications involve also peripheral organs mainly a stimulant of secretions or gastrointestinal motricity.

The compounds of the invention are particularly useful for the treatment of CNS disorders of aged persons.

Additionally, said antagonists or inverse agonists may also be useful in treating and/or preventing epilepsy.

As used herein, "epilepsy" denotes a brain disorder in which clusters of nerve cells, or neurons, in the brain sometimes signal abnormally. Epilepsy is also known as a seizure disorder. A seizure is a sudden surge of electrical activity in the brain. Epilepsy is usually diagnosed after a person has had at least two seizures that were not caused by some known medical condition like alcohol withdrawal or extremely low blood sugar.

Preferably, epilepsy is selected from the group consisting in absence epilepsy, in children and adults, pharmaco-resistant temporal lobe seizures, and photosensitive seizures.

Additionally, the present application also concerns the use of the compounds of the invention for treating and/or preventing Parkinson's disease, obstructive sleep apnea (OSA), dementia with Lewy bodies and/or vascular dementia and in particular the treatment of their symptoms thereof.

As used herein, "obstructive sleep apnea" (also referred to herein as "OSA") denotes a breathing disorder that occurs primarily during sleep with consequences that may persist throughout the waking hours in the form of sleepiness. This increasingly well-recognized disease is characterized by periodic collapse of the upper airway during sleep with apneas (periodic cessation of breathing), hypopneas (repetitive reduction in breathing) or a continuous or sustained reduction in ventilation and excessive daytime sleepiness, neurocognitive defects and depression. It affects almost every system in the body, resulting namely in increased incidence of cardiovascular disorders (Qureshi and Ballard, J. Allergy and *Clin. Immunol.*, 2003, 112, 643). There is no known pharmacological treatment for OSA.

"Parkinson's disease" ("PD") is mainly associated with a degeneration of dopaminergic neurons in the nigrostriatal tract from which derive the motor impairments and neuropsychiatric disorders characteristic of the disease. Whereas some other aminergic neuron classes might be affected in the parkinsonian brain, post-mortem neurochemical and immunohistochemical studies have shown that histaminergic neurons are completely spared from the degeneration process (Garbarg et al., *Lancet*, 1983, 1, 74; Nakamura et al., *Neurology*, 1996, 4, 1693). In addition, in a model of "Parkinsonian" rat, in which the nigrostriatal dopaminergic neurons had been previously destroyed by unilateral administration of the neurotoxin 6-hydroxydopamine, the effect of the antiparkinsonian drug levodopa on the turning behaviour, a reflect of its antiparkinsonian activity, was not modified by co-administration of thioperamide, a prototypical $H_3R$ antagonist/inverse agonist (Huotary et al., *Parkinsonism Relat. Disord.*, 2000, 6, 159). This absence of effect is not attributable to either an absence of $H_3R$ sites in the nigrostriatal complex where, on the contrary, they abund (Pillot et al., *Neuroscience*, 2002, 114, 176) or a disappearance of $H_3R$ sites as a result of the neuronal degeneration process, since the number of these sites is, on the contrary, elevated in the same animal model (Ryu et al., *Neurosci. Letters*, 1994, 178, 19). Taken together these findings suggested the lack of therapeutic interest of this class of drugs in the management of PD.

In addition to the major signs of PD in the movement initiation and control which constitute the core of the disease, it has become apparent during the last decades that a large proportion (as large as 74-81%) of PD patients display sleep and vigilance disorders (Garcia-Borreguero et al., *Sleep Med. Rev.*, 2003, 7, 115). These include disorders of sleep initiation and maintenance, sleep fragmentation, parasomnias (including nocturnal hallucinations), sleep disordered breathing and excessive daytime sleepiness (including "sleep attacks", i.e. inappropriate and unintended falls into sleep while in daytime activity). It is not entirely clear whether this group of disorders is purely related to the PD itself or whether there is also some participation of the treatment by direct or indirect dopaminergic agonists. The treatment of this class of disorders, which may all result from a loss of circadian rythmicity, is poorly efficient: for instance, modafinil treatment of excessive daytime sleepiness was tried with limited success and the indication for this stimulant drug of essentially unknown mechanism of action has not been recognized by health authorities.

PD refers to idiopathic PD or idiopathic parkinsonism described by James Parkinson in 1817. The clinical tetrad of PD includes tremor at repose, bradykinesia (slowness of voluntary movement) or akinesia (reduced or absent movement), cogwheel or leadpipe rigidity, and postural impairment causing difficulty in turning and a stooped posture. The pathologic hallmark is the presence of intracytoplasmic eosinophilic inclusions (Lewy bodies) in addition to loss of neurons in the substantia nigra pars compacta. In addition to the major signs of PD in the movement initiation and control which constitute the core of the disease, a large proportion of PD patients display sleep and vigilance disorders. These "sleep and vigilance disorders associated with PD" include in particular insomnia, disorders of sleep initiation and maintenance, sleep fragmentation, parasomnias, sleep disordered breathing, excessive daytime sleepiness (including "sleep attacks") and circadian dysrhythmia (inversion of sleep-wake rhythm).

Dementia with Lewy bodies (DLB) results from the accumulation of such bodies in the cortex (whereas their accumulation in the nigro-striatal complex is observed in PD, a related degenerative disease). It is characterized by cognitive impairment, aftentional disturbances, hallucinations, depression and sleep disorders.

Vascular dementia, the second most frequent cause of dementia, after Alzheimer's disease, is characterized by acute loss of memory, orientation and executive functions and is often associated with demonstrable cerebrovascular lesions in patients suffering from hypertension, diabetes, hyperlipidemia, sleep apnea for several years.

The compounds of the invention can also be useful for the treatment and/or prevention of vertigo, motion sickness, obesity, diabetis and so-called "metabolic syndrome". Metabolic syndrome was first defined as syndrome X by Reaven (Diabetes 1988, 37, 1595-607). It refers to a cluster of metabolic disorders such as diabetes, impaired glucose tolerance, insulin resistance, hyperinsulinemia, hypertriglyceridemia, dyslipidemia, low HDL-cholesterol, hypertension, microalbuminuria, obesity, inflammation, cardiovascular disorders and/or abnormalities of fibrinolysis and of coagulation.

Additionally, the compounds of the invention can be useful for treating and/or preventing sleep disorders, stress, psychotropic disorders, convulsion, depression, narcolepsy, disorders of the hypothalamohypophyseal secretion, the cerebral circulation and/or immune system.

The present invention also concerns the corresponding methods of treatment comprising the administration of a compound of the invention together with a pharmaceutically acceptable carrier or excipient to a patient in the need thereof.

The identification of those subjects who are in need of treatment of herein-described diseases and conditions is well within the ability and knowledge of one skilled in the art. A clinician skilled in the art can readily identify, by the use of clinical tests, physical examination and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient, and the route of administration.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any diluents, adjuvants, excipients, or vehicles, such as preserving agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with a neuropsychological disorder. Preferably, the patient is a human.

In general terms, the compounds of this invention may be provided in an aqueous physiological buffer solution containing 0.1 to 10% w/v compound for parenteral administration. Typical dose ranges are from 1 μg/kg to 0.1 g/kg of body weight per day; a preferred dose range is from 0.01 mg/kg to 10 mg/kg of body weight per day. A preferred daily dose for adult humans includes 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, formulation of the compound excipient and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Preferably the unit dose range is from 1 to 500 mg administered one to four times a day, and even more preferably from 10 mg to 300 mg, two times a day. Compounds provided herein can be formulated into pharmaceutical compositions by admixture with one or more pharmaceutically acceptable excipients. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via transdermal patches.

The compositions may conveniently be administered in unit dosage form and may be prepared by any of the methods well known in the pharmaceutical art, for example, as described in *Remington: The Science and Practice of Pharmacy*, $20^{th}$ ed.; Gennaro, A. R., Ed.; Lippincott Williams & Wilkins: Philadelphia, Pa., 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description in the following examples.

EXAMPLE 1

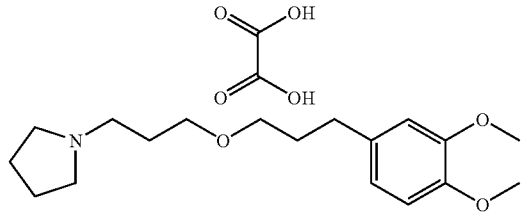

1-{3-[3-(3,4-dimethoxyphenyl)propoxy] propyl}pyrrolidine, oxalate

A To a solution of 1-(3-hydroxypropyl)pyrrolidine (631 mg) in toluene (10 mL) stirred at a temperature close to 0° C. is added sodium hydride (208 mg, 60% wt in paraffin). The mixture is stirred for three hours at room temperature, cooled to a temperature close to 0° C. and 3-(3,4-dimethoxyphenyl) propan-1-ol mesylate (750 mg), 15-crown-5 (30 μL), tetrabutylammonium iodide (8 mg) are added. The mixture is heated at reflux for 30 min, stirred overnight at room temperature and diluted with diethyl oxide. The organic layer is washed twice with water, dried over magnesium sulphate, concentrated under reduced pressure and purified by chromatography over silica gel with dichloromethane/methanol 94/6 as eluent. Fractions containing the expected product are pooled, concentrated under reduced pressure, dissolved in diethyl oxide and salted with a solution of 68.8 mg of oxalic acid in 1 mL of acetone. The precipitate is filtered, rinsed with diethyl oxide and dried to give 110 mg of 1-{3-[3-(3,4-dimethoxyphenyl) propoxy]propyl}-pyrrolidine, oxalate as a solid melting at 78-79° C.

$^1$H NMR oxalate (DMSO)

6.79 (m, 3H, arom), 3.70 (s, 3H, OCH$_3$), 3.68 (s, 3H, OCH$_3$), 3.35 (m, 4H, 2 CH$_2$O), 3.12 (m, 6H, 3 CH$_2$N), 2.50 (m, 2H, CH$_2$Ar), 1.82 (m, 8H, 4 CH$_2$)

B 3-(3,4-dimethoxyphenyl)propan-1-ol mesylate can be prepared as follows

To a solution of 3-(3,4-dimethoxyphenyl)propan-1-ol (2.35 g) in triethylamine (2.5 mL) and dichloromethane (50 mL) stirred at a temperature close to 0° C. is added dropwise methanesulfonyl chloride (1.7 mL). The mixture is stirred overnight, concentrated under reduced pressure, dissolved in ethyl acetate. The organic layer is washed successively with water, a 0.1N aqueous hydrochloric solution, a saturated aqueous sodium hydrogenocarbonate solution and water, dried over magnesium sulphate, concentrated under reduced pressure and purified by chromatography over silica gel with heptane/ethyl acetate 7/3 as eluent. Fractions containing the expected product are pooled and concentrated under reduced pressure to give 3 g of 3-(3,4-dimethoxyphenyl)propan-1-ol mesylate used without further purification.

3-(3,4-dimethoxyphenyl)propan-1-ol can be prepared according to the procedure described by B. Frydman and V. Deulafeu, *Tetrahedron* 18 1063-72 (1962).

EXAMPLE 2

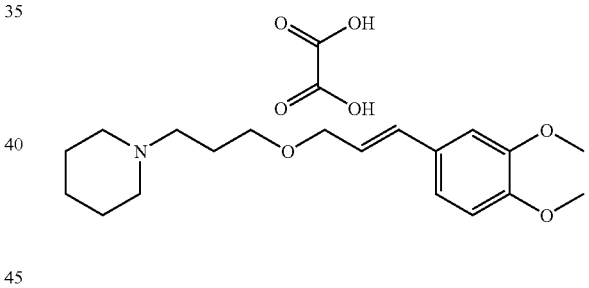

trans-1-{3-[3-(3,4-dimethoxyphenyl)allyloxy] propyl}piperidine, oxalate

To a solution of 3-(3,4-dimethoxyphenyl)prop-2-en-1-ol (270 mg) in dimethyl-sulfoxyde (4 mL) are added successively powdered potassium hydroxyde (175 mg 85% wt) and, portionwise, 1-(3-chloropropyl)piperidine, hydrochloride (250 mg). The mixture is stirred overnight at room temperature, then hydrolysed with water (80 mL). The solution is extracted twice with ethyl acetate (20 mL). The combined extracts are washed twice with water (10 mL), dried over magnesium sulphate, concentrated under reduced pressure and purified by chromatography over silica gel with a gradient dichloromethane/methanol from 98/2 to 90/10. Fractions containing the expected product are pooled, concentrated under reduced pressure, dissolved in 10 mL of dichloromethane, filtered over Millipore membrane and concentrated under reduced pressure. The base thus obtained is dissolved in 2 mL of ethanol and 100 μL of diethyl oxide. A solution of 88 mg of oxalic acid in 2 mL of ethanol is added. The precipitate that appears is filtered, washed with diethyl oxide and dried under reduced pressure at a temperature close to 40 C to give 185 mg of trans-1-{3-[3-(3,4-dimethoxyphenyl)allyloxy]propyl}piperidine, oxalate as a white powder melting at 111-112° C.

¹H NMR oxalate (DMSO)

7.04 (s, 1H, arom), 6.89 (m, 2H, arom), 6.50 (d, J=16 Hz, 1H, ArCH=), 6.21 (dt, J=16 Hz, J=5.7 Hz, 1H, CH=), 4.03 (d, J=5.7 Hz, 2H, OCH₂), 3.74 (s, 3H, OCH₃), 3.71 (s, 3H, OCH₃), 3.44 (t, J=5.8 Hz, 2H, OCH₂), 3.00 (m, 6H, 3 CH₂N), 1.88 (m, 2H, CH₂), 1.70 (m, 4H, 2 CH₂), 1.49 (m, 2H, CH₂)

3-(3,4-dimethoxyphenyl)prop-2-en-1-ol can be prepared as described by A. Srikrishna et al. Syn. Commun. 31(15) 2357-64 (2001) or M.M. Ponpiporn et al., *J. Med. Chem.* 27(3) 309-12 (1986).

EXAMPLE 3

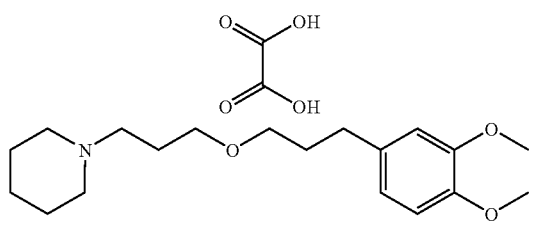

1-{3-[3-(3,4-dimethoxyphenyl)propoxy]propyl}piperidine, oxalate

Following the procedure described in example 1§A, but starting from 1-(3-hydroxypropyl)piperidine (1 g), sodium hydride (0.28 g, 60% wt in paraffin), 3-(3,4-dimethoxyphenyl)propan-1-ol mesylate (0.96 g), 15-crown-5 (30 μL), tetrabutyl-ammonium iodide (15 mg) and toluene (10 mL) affords, after salt formation with oxalic acid, 230mg of 1-{3-[3-(3,4-dimethoxyphenyl)propoxy]-propyl}piperidine, oxalate as a solid melting at 111° C.

¹H NMR oxalate (DMSO)

7.81 (d, J=8.1 Hz, 1H, arom), 6.75 (s, 1H, arom), 6.66 (d, J=8.1 Hz, 1H, arom), 3.70 (s, 3H, OCH₃), 3.68 (s, 3H, OCH₃), 3.38 (t, J=5.9 Hz, 2H, CH₂O), 3.32 (t, J=6.4 Hz, 2H, CH₂O), 2.98 (m, 6H, 3 CH₂N), 2.51 (m, 2H, CH₂Ar), 1.90-1.65 (m, 8H, 4CH₂), 1.49 (m 2H, CH₂)

EXAMPLE 4

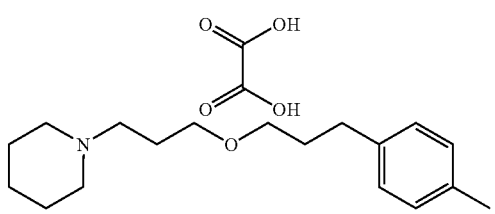

1-{3-[3-(4-methylphenyl)propoxy]propyl}piperidine, oxalate

A Following the procedure described in example 1§A, but starting from 1-(3-hydroxypropyl)piperidine (1 g), sodium hydride (313 mg, 60% wt in paraffin), 3-(4-methylphenyl)propan-1-ol mesylate (911 mg), 15-crown-5 (30 μL), tetrabutyl-ammonium iodide (8 mg) and toluene (11 mL) affords, after salt formation with oxalic acid, 90 mg of 1-{3-[3-(3,4-dimethoxyphenyl)propoxy]propyl}pyrrolidine, oxalate as a white solid melting at 109-110° C.

¹H NMR oxalate (DMSO)

7.06 (m, 4H, arom), 3.37 (t, J=5.8 Hz, 2H, CH₂O), 3.31 (t, J=6.4 Hz, 2H, CH₂O), 3.00 (m, 6H, 3 CH₂N), 2.56 (m, 2H, CH₂Ar), 2.23 (s, 3H, ArCH₃), 1.84 (m, 2H, CH₂),1.75 (m, 6H, 3 CH₂), 1.49 (m, 2H, CH₂)

B 3-(4-methylphenyl)propan-1-ol mesylate can be Prepared as Follows

Following the procedure described in example 1§B, but starting from 3-(4-methylphenyl)propan-1-ol (6.02 g), triethylamine (2.9 mL), methanesulfonyl chloride (3.67 mL) and dichloromethane (39 mL), affords 3-(4-methylphenyl)propan-1-ol mesylate (3.4 g) used without further purification.

3-(4-methylphenyl)propan-1-ol can be prepared according to the procedure described by H. Oelschlaeger, *Arch. Pharm. Ber. Dtsch Pharm. Ges.* 293 441-51(1960) or S. A. Glover et al., *Tetrahedron* 46(20) 7247-62 (1990).

EXAMPLE 5

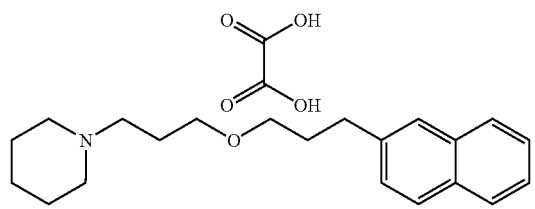

1-{3-[3-(2-naphtyl)propoxy]propyl}piperidine, oxalate

A Following the procedure described in example 1§A, but starting from 1-(3-hydroxypropyl)piperidine (1 g), sodium hydride (0.28 g, 60% wt in paraffin), 3-(2-naphtyl)propan-1-ol mesylate (0.93 g), 15-crown-5 (30 μL), tetrabutylammonium iodide (15 mg) and toluene (10 mL) affords, after salt formation with oxalic acid, 260 mg of 1-{3-[3-(2-naphtyl)propoxy]propyl}piperidine, oxalate as a solid melting at 136° C.

¹H NMR oxalate (DMSO)

7.82 (m, 3H, arom), 7.46 (s, 1H, arom), 7.40 (m, 3H, arom), 3.34 (m, 4H, 2 CH₂O), 3.00 (m, 6H, 3 CH₂N), 2.76 (t, J=7.3 Hz, 2H, CH₂Ar), 1.86 (m, 4H, 2 CH₂), 1.66 (m, 4H, 2 CH2), 1.49 (m, 2H, CH₂)

B 3-(2-naphtyl)propan-1-ol mesylate can be Prepared as Follows

Following the procedure described in example 1§B, but starting from 3-(2-naphtyl)propan-1-ol (11.7 mmol), triethylamine (2.5 mL), methanesulfonyl chloride (1.7 mL) and dichloromethane (50 mL), affords 1.7 g of 3-(2-naphtyl)propan-1-ol mesylate used without further purification.

3-(2-naphtyl)propan-1-ol can be prepared as described by R. C. Hahn et al. J. Amer. Chem. Soc. 91(13) 3558-66 (1969) or A. D. Gribble et al. J. Med. Chem. 39(18) 3569-84(1996).

EXAMPLE 6

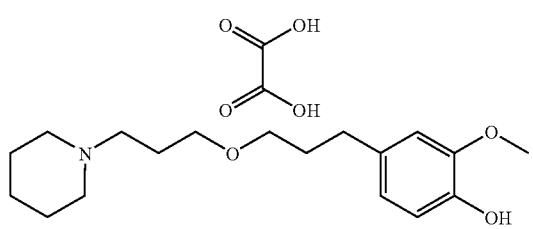

1-{3-[3-(4-hydroxy-3-methoxyphenyl)propoxy]propyl}piperidine, oxalate

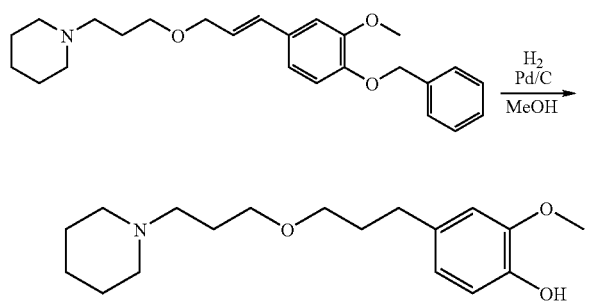

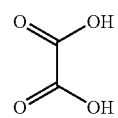

A A suspension of 10% palladium on charcoal (25 mg) in a solution of trans-1-{3-[3-(4-benzyloxy-3-methoxyphenyl)allyloxy]propyl}piperidine (340 mg containing 28% wt dimethylsufoxide) in methanol (2.5 mL) is stirred overnight at room temperature under an atmosphere of dihydrogene. The suspension is filtered over a clarcel pad and the filtrate concentrated under reduced pressure. The product is dissolved in diethyl oxide and a solution of oxalic acid (61 mg) in acetone is added. The precipitate is filtered, washed with diethyl oxide and dried under vacuum to afford 150 mg of 1-{3-[3-(4-hydroxy-3-methoxyphenyl)propoxy]propyl}-piperidine, oxalate as a white solid melting at 110-111° C.

$^1$H NMR oxalate (DMSO)

7.70 (d, J=1.5 Hz, 1H, arom), 6.63 (d, J=8 Hz, 1H, arom), 6.53 (dd, J=8 Hz, J=1.5 Hz, 1H, arom), 3.71 (s, 3H, OCH$_3$), 3.37 (d, J=6.5 Hz, 2H, CH$_2$O), 3.32 (d, J=6.4 Hz, 2H, CH$_2$O), 3.00 (m, 6H, 3 CH$_2$N), 2.50 (m, 2H, CH$_2$Ar), 1.85 (m, 2H, CH$_2$), 1.72 (m, 6H, 3 CH$_2$), 1.49 (m, 2H, CH$_2$)

B trans-1-{3-[3-(4-benzyloxy-3-methoxyphenyl)allyloxy]propyl}piperidine can be Prepared as Follows Following the procedure described in example 2, but starting from 3-(4-benzyloxy-3-methoxyphenyl)prop-2-en-1-ol (600 mg), potassium hydroxide (308 mg 85% wt) and 1-(3-chloropropyl)piperidine, hydrochloride (440 mg) in dimethylsufoxide (5 mL) affords 740 mg of trans-1-{3-[3-(4-benzyloxy-3-methoxyphenyl)-allyloxy]-propyl}piperidine containing 28% wt/wt DMSO used without any further purification. 3-(4-benzyloxy-3-methoxyphenyl)prop-2-en-1-ol can be prepared according to S. V. Reddy et al Chem. Lett. 32(11) 1038-9 (2003) or W. Gu et al Tetrahedron Lett. 41(32) 6079-82 (2000).

EXAMLE 7

1-{3-[3-(4-fluorophenyl)propoxy]propyl}pyrrolidine, oxalate

A suspension of platinum dioxide (300 mg) in a solution of trans-1-{3-[3-(4-fluorophenyl)allyloxy]propyl}pyrrolidine (330 mg) in N,N-dimethylformamide (3 mL) is stirred overnight at room temperature under an atmosphere of dihydrogene. An additional amount of platinum dioxide is added and the suspension is stirred for 24 hours at room temperature under an atmosphere of dihydrogene. The suspension is filtered over a celite pad and rinsed with ethyl acetate. Ethyl acetate is evaporated from the filtrate, platinum hydroxide (190 mg) is added and the suspension is stirred for 48 hours at room temperature under an atmosphere of dihydrogene. The suspension is filtered over a celite pad, rinsed with ethyl acetate, concentrated under reduced pressure and dissolved in a mixture of ethanol (2 mL) and diethyl oxide (200 µL). A solution of oxalic acid (58 mg) in ethanol (2 mL) is added. The mixture is concentrated under reduced pressure and suspended in diethyl oxide. The precipitate is filtered, rinsed with diethyl ether, dissolved in water (5 mL). The aqueous layer is made alkaline with ammonia and extracted twice with diethyl oxide (10 mL). The organic extracts are pooled, dried over magnesium sulphate, concentrated under reduced pressure and purified by chromatography over silica gel with a gradient dichloromethane/methanol/ammonia from 99/10/0.1 to 92/2/0.2. Fractions containing the expected product are pooled, concentrated under reduced pressure, dissolved in diethyl oxide (2 mL). A solution of oxalic acid (21 mg) in acetone is added and the precipitate that appears is filtered and dried under reduced pressure at 40° C. under a film of diethyl oxide to give 96 mg of 1-{3-[3-(4-fluorophenyl)propoxy]propyl}pyrrolidine, oxalate as a white solid melting at 106° C.

$^1$H NMR oxalate (DMSO)

7.19 (m, 2H, arom), 7.06 (m, 2H, arom), 3.33 (m, 4H, 2 CH$_2$O), 3.08 (m, 6H, 3 CH$_2$N), 2.57 (m, 2H, CH$_2$Ar), 1.77 (m, 8H, 4 CH$_2$)

B

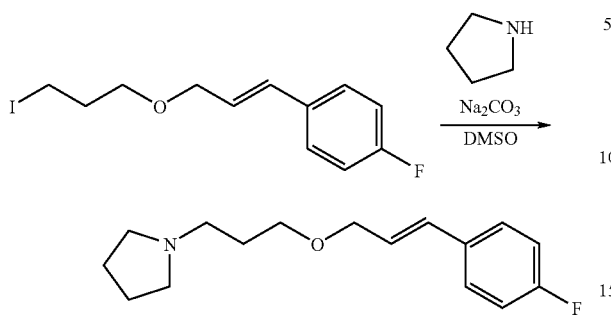

trans-1-{3-[3-(4-fluorophenyl)allyloxy]propyl}pyrrolidine can be Prepared as Follows A suspension of sodium carbonate (414 mg) in a solution of trans-4-fluoro-1-[3-(3-iodopropoxy)prop-1-en-1-yl]phenyl (250 mg) in piperidine (231 µL) and dimethylsulfoxide (2 mL) is stirred overnight at room temperature. Water (10 mL) is added and the mixture extracted twice with diethyl oxyde (10 mL), washed with water (10 mL), dried over magnesium sulfate, filtered and concentrated under reduced pressure to give 168 mg of trans-1-{3-[3-(4-fluorophenyl)allyloxy]-propyl}pyrrolidine used without further purification.

Rf TLC (dichloromethane/methanol/ammonia 90/10/1)=0.75

C trans-4-fluoro-1-[3-(3-iodopropoxy)prop-1-en-1-yl]phenyl can be Prepared as Follows

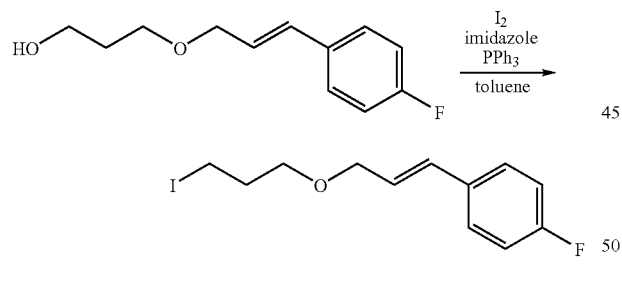

A solution of trans-3-[3-(4-fluorophenyl)allyloxy]propanol (800 mg), triphenyl-phosphine (1.5 g) and imidazole (389 mg) in toluene is heated at a temperature close to 60° C. Diiodine (1.29 g) is added portionwise. The mixture is stirred for an additional hour at a temperature close to 60° C., then cooled back to room temperature. A saturated aqueous solution of sodium bicarbonate (5 mL) is added followed by diiodine until persisting coloration. The organic layer is separated by decantation, dried over magnesium sulfate and concentrated under reduced pressure to give 940 mL of trans-4-fluoro-1-[3-(3-iodopropoxy)prop-1-en-1-yl]phenyl as a pale yellow oil.

Rf TLC (heptane/ethyl acetate 1/1)=0.8

D

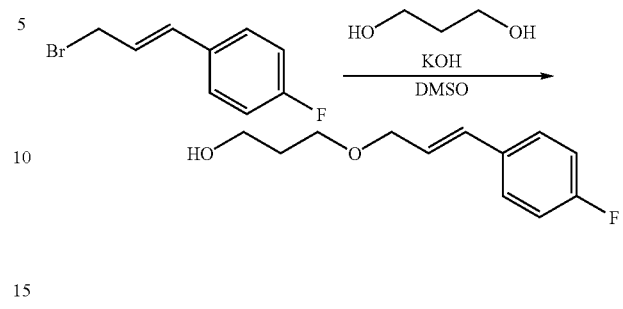

trans-3-[3-(4-fluorophenyl)allyloxy]propanol can be Prepared as Follows

A solution of trans-1-(3-bromoprop-1-en-1-yl)-4-fluorophenyl (12 mmol) in dimethyl-sufoxide (5 mL) is added to a suspension of potassium hydroxide (1.41 g, 85% wt) in a mixture of 1,3-propanediol (1.85 mL) and dimethylsulfoxide (9 mL) cooled at a temperature close to 0° C. The mixture is stirred for an additional hour at room temperature, poored onto ice cold water (50 mL) and extracted with ethyl acetate (three time 50 mL). The organic layers are pooled, washed twice with water (30 mL), dried over magnesium sulfate, filtered, concentrated under reduced pressure, purified by chromatography over silica gel with a gradiant heptane/ethyl acetate from 100/0 to 60/40. Fractions containing the expected product are pooled and concentrated under reduced pressure to give 800 mg of trans-3-[3-(4-fluorophenyl)allyloxy]propanol as an orange oil.

Rf TLC (heptane/ethyl acetate 1/1)=0.23 trans-1-(3-bromoprop-1-en-1-yl)-4-fluorophenyl can be prepared as described by H. Jendralla et al J. Med. Chem. 34(10) 2962-3 (1991) or R. C. Lamb et al J. Org. Chem. 31 147-53 (1966)

EXAMPLE 8

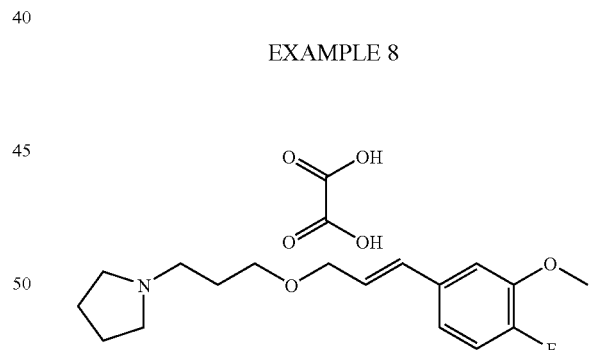

trans-1-{3-[3-(4-fluoro-3-methoxyphenyl)allyloxy]propyl}pyrrolidine, oxalate Following the procedure described in example 2, but starting from 3-(4-fluoro-3-methoxyphenyl)prop-2-en-1-ol (600 mg), potassium hydroxide (456 mg, 85% wt) and 1-(3-chloropropyl)pyrrolidine, hydrochloride (618 mg) in dimethylsufoxide (5 mL) affords 40 mg of trans-1-{3-[3-(4-fluoro-3-methoxyphenyl)allyloxy]-propyl}pyrrolidine, oxalate as a solid melting at 143-144° C.

$^1$H NMR oxalate (DMSO)

7.23 (m, 1H, arom), 7.16 (m, 1H, arom), 6.98 (m, 1H, arom), 6.54 (d, J=16 Hz, 1H, ArCH=), 6.32 (dt, J=16 Hz, J=5.7 Hz, 1H, CH=), 4.06 (d, J=5.7 Hz, 2H, OCH$_2$), 3.83 (s, 3H OCH$_3$), 3.46 (t, J=6.0 Hz, 2H, OCH$_2$), 3.12 (m, 6H, 3 CH$_2$N), 1.88 (m, 6H, 3 CH$_2$)

EXAMPLE 9

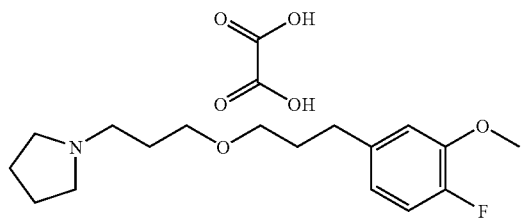

1-{3-[3-(4-fluoro-3-methoxyphenyl)propoxy]propyl}pyrrolidine, oxalate Following the procedure described in example 7, but with trans-1-{3-[3-(4-fluoro-3-methoxyphenyl)allyloxy]propyl}pyrrolidine (185 mg) and platinum dioxide (74 mg) in N,N-dimethylformamide (2 mL), gives after salt formation with oxalic acid, 110 mg of 1-{3-[3-(4-fluoro-3-methoxyphenyl)propoxy]propyl}pyrrolidine, oxalate as a beige solid melting at 87-88° C.

$^1$H NMR oxalate (DMSO)

7.05 (m, 1H, arom), 6.95 (m, 1H, arom), 6.70 (m, 1H, arom), 3.79 (s, 3H, OCH$_3$), 3.38 (t, J=6 Hz, 2H, CH$_2$O), 3.35 (t, J=6.4 Hz, 2H, CH$_2$O), 3.08 (m, 6H, 3 CH$_2$N), 2.56 (t, J=7.4 Hz, 2H, CH$_2$Ar), 1.79 (m, 8H, 4CH$_2$)

EXAMPLE 10

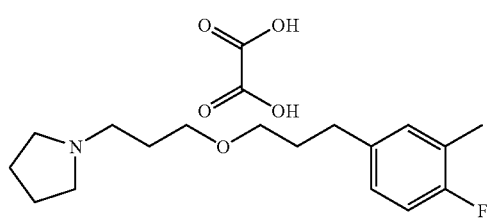

1-{3-[3-(4-fluoro-3-methylphenyl)propoxy]propyl}pyrrolidine, oxalate

A Following the procedure described in example 7, but with trans-1-{3-[3-(4-fluoro-3-methylphenyl)allyloxy]propyl}pyrrolidine (200 mg) and platinum dioxide (73 mg) in N,N-dimethylformamide (1.8 mL), gives after salt formation with oxalic acid, 150 mg of 1-{3-[3-(4-fluoro-3-methylphenyl)propoxy]-propyl}pyrrolidine, oxalate as a white solid melting at 92-93° C.

$^1$H NMR oxalate (DMSO)

7.06 (m, 1H, arom), 7.00 (m, 2H, arom), 3.38 (t, J=6 Hz, 2H, CH$_2$O), 3.32 (t, J=6.4 Hz, 2H, CH$_2$O), 3.20 (m, 4H, 2 CH$_2$N), 3.09 (m, 2H, CH$_2$N), 2.53 (t, J=7.3 Hz, 2H, CH$_2$Ar), 2.17 (s, 3H, CH$_3$), 1.80 (m, 8H, 4CH$_2$)

B trans-1-{3-[3-(4-fluoro-3-methylphenyl)allyloxy]propyl}pyrrolidine can be Prepared as Follows Following the procedure described in example 2, but starting from trans-3-(4-fluoro-3-methylphenyl)prop-2-en-1-ol (710 mg), potassium hydroxide (592 mg, 85% wt) and 1-(3-chloropropyl)pyrrolidine, hydrochloride (802 mg) in dimethylsufoxide (6 mL) affords 280 mg of trans-1-{3-[3-(4-fluoro-3-methylphenyl)allyloxy]propyl}-pyrrolidine.

$^1$H NMR oxalate (DMSO)

7.17 (m, 2H, arom), 6.94 (t, J=9.1 Hz, 1H, arom), 6.53 (d, J=15.9 Hz, 1H, ArCH=), 6.19 (dt, J=15.9 Hz, J=5.9 Hz, 1H, CH=), 4.12 (d, J=5.9 Hz, 2H, OCH$_2$), 3.54 (t, J=6.6 Hz, 2H, OCH$_2$), 2.52 (m, 6H, 3 CH$_2$N), 2.27 (s, 3H CH$_3$), 1.82 (m, 6H, 3 CH$_2$)

C

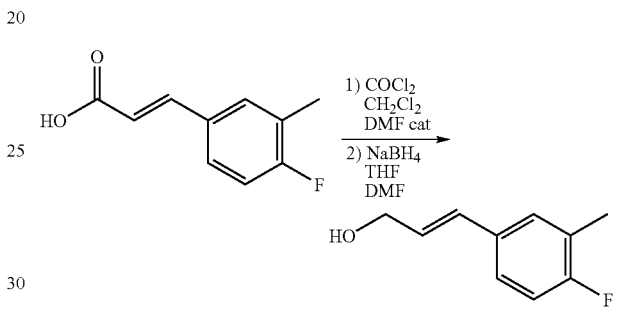

trans-3-(4-fluoro-3-methylphenyl)prop-2-en-1-ol can be Prepared as Follows

A mixture of trans-3-(4-fluoro-3-methylphenyl)prop-2-enoic acid (6.18 g) and oxalyl chloride (3.72 mL) in dichloromethane (40 mL) containing N,N-dimethylformamide (60 μL) is stirred at room temperature for three hours, concentrated under reduced pressure and redissolved in tetrahydrofurane (50 mL). The solution is maintained at a temperature below −8° C. during the addition of a suspension of sodium borohydride (2.9 g) in N,N-dimethylformamide (15 mL). The mixture is stirred for one hour at a temperature close to −12° C., hydrolysed by the successive addition of water (10 mL) and 1N hydrochloric acid and extracted with ethyl acetate. The organic layers are pooled, washed with water, dired over magnesium sulfate, concentrated under reduced pressure and purified by chromatography over silica gel, with heptane/ethyl acetate 3/1 as eluant, to give 710 mg of trans-3-(4-fluoro-3-methylphenyl)prop-2-en-1-ol as a colorless oil used without further purification.

trans-3-(4-fluoro-3-methylphenyl)prop-2-enoic acid is Commercially Available

EXAMPLE 11

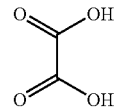

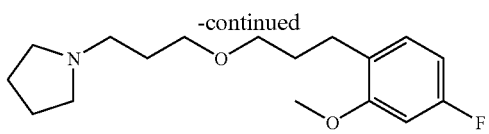

1-{3-[3-(4-fluoro-2-methoxyphenyl)propoxy]propyl}pyrrolidine, oxalate

A Following the procedure described in example 7, but with trans-1-{3-[3-(4-fluoro-2-methoxyphenyl)allyloxy]propyl}pyrrolidine (210 mg) and platinum dioxide (90 mg) in N,N-dimethylformamide (4 mL), gives after salt formation with oxalic acid, 145 mg of 1-{3-[3-(4-fluoro-2-methoxyphenyl)propoxy]propyl}-pyrrolidine, oxalate as a white solid.

¹H NMR oxalate (DMSO)
7.08 (t, J=8 Hz, 1H, arom), 6.81 (dd, J=11.5 Hz, J=2.5 Hz, 1H, arom), 6.64 (td, J=14.4 Hz, J=2.5Hz, 1H, arom), 3.75 (s, 3H, OCH₃), 3.37 (t, J=6 Hz, 2H, CH₂O), 3.32 (t, J=6.4 Hz, 2H, 2 CH₂O), 3.19 (m, 4H, 2 CH₂N), 3.08 (m, 2H, CH₂N), 2.51 (t, J=7.3 Hz, 2H, CH₂Ar), 1.86 (m, 4H, 2CH₂), 1.68 (m, 4H 2 CH₂)

B trans-1-{3-[3-(4-fluoro-2-methoxyphenyl)allyloxy]propyl}pyrrolidine can be Prepared as Follows Following the procedure described in example 2, but starting from trans-3-(4-fluoro-2-methoxyphenyl)prop-2-en-1-ol (400 mg), potassium hydroxide (308 mg 85% wt) and 1-(3-chloropropyl)pyrrolidine, hydrochloride (417 mg) in dimethylsulfoxide (4 mL) affords 320 mg of trans-1-{3-[3-(3-methoxyphenyl)allyloxy]propyl}pyrrolidine as a colorless oil used without further purification.

C trans-3-(4-fluoro-2-methoxyphenyl)prop-2-en-1-ol can be Prepared as Follows Following the procedure described in example 10§C, but starting from trans-3-(4-fluoro-2-methoxyphenyl)prop-2-enoic acid (1.28 g), oxalyl chloride (0.7 mL), dichloromethane (9 mL) and N,N-dimethylformamide (13 µL) and then tetrahydro-furane (10 mL), sodium borohydride (0.55 g) and N,N-dimethylformamide (4 mL) affords 815 mg of trans-3-(4-fluoro-2-methoxyphenyl)-prop-2-en-1-ol used without further purification.

trans-3-(4-fluoro-2-methoxyphenyl)prop-2-enoic acid is Commercially Available

EXAMPLE 12

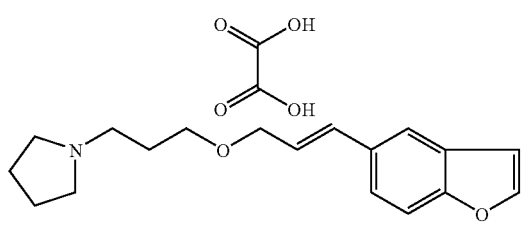

trans-1-{3-[3-(benzofuran-5-yl)allyloxy]propyl}pyrrolidine, oxalate

A Following the procedure described in example 2, but starting from trans-3-(benzofuran-5-yl)prop-2-en-1-ol (600 mg), potassium hydroxide (477 mg 85% wt) and 1-(3-chloropropyl)pyrrolidine, hydrochloride (647 mg) in dimethylsulfoxide (5 mL) affords 120 mg of trans-1-{3-[3-(benzofuran-5-yl)allyloxy]propyl}pyrrolidine, oxalate as a white solid.

¹H NMR oxalate (DMSO)
7.96 (d, J=2.0 Hz, 1H, arom), 7.68 (s, 1H, arom), 7.53 (d, J=8.5 Hz, 1H, arom), 7.43 (d, J=8.5 Hz, 1H, arom), 6.91 (d, J=2.0 Hz, 1H, arom), 6.68 (d, J=16 Hz, 1H, ArCH=), 6.32 (dt, J=16 Hz, J=5.9 Hz, 1H, CH=), 4.08 (d, J=5.9 Hz, 2H, OCH₂), 3.47 (t, J=5.9 Hz, 2H, OCH₂), 3.16 (m, 6H, 3 CH₂N), 1.86 (m, 6H, 3 CH₂)

trans-3-(benzofuran-5-yl)prop-2-en-1-ol can be prepared as described by T. Hiraiwa et al DE3906920 (Sep. 14, 1989).

EXAMPLE 13

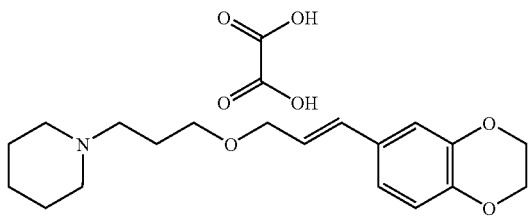

1-{3-[3-(2,3-dihydrobenzo[1,4]dioxin-6-yl)allyl]oxy}propyl)piperidine, oxalate A Following the procedure described in example 7§B, but starting from trans-2,3-dihydro-6-[3-(3-iodopropoxy)prop-1-en-1-yl]benzo[1,4]dioxine (200 mg), piperidine (165 µL) and sodium carbonate (294 mg) in dimethylsulfoxide (1.8 mL) affords 172 mg of 1-{3-[3-(2,3-dihydrobenzo[1,4]dioxin-6-yl)allyl]oxy}propyl)piperidine, oxalate melting at 120° C.

¹H NMR oxalate (DMSO)
6.91 (m, 2H, arom), 6.78 (d, J=8.1 Hz, 1H, arom), 6.45 (d, J=15.7 Hz, 1H ArCH=), 6.13 (m, 1H, CH=), 4.20 (s, 4H, OCH₂CH₂O), 4.02 (d, J=5.7 Hz, 2H, OCH₂), 3.43 (t, J=5.9 Hz, 2H, OCH₂), 3.03 (m, 6H, 3 CH₂N), 1.87 (m, 2H, CH₂), 1.67 (m, 4H, 2 CH₂),1.49 (m, 2H, CH₂)

B trans-2,3-dihydro-6-[3-(3-iodopropoxy)prop-1-en-1-yl]benzo[1,4]dioxine can be Prepared as Follows Following the procedure described in example 7§C, but starting from trans-2,3-dihydro-6-[3-(3-hydroxypropoxy)prop-1-en-1-yl]benzo[1,4]dioxine (280 mg), triphenylphosphine (455 mg), imidazole (114 mg) and diiodine (355 mg) in toluene (2.6 mL) affords 780 mg of trans-2,3-dihydro-6-[3-(3-iodopropoxy)prop-1-en-1-yl]benzo[1,4]dioxine as a clear oil used without further purification.

C trans-2,3-dihydro-6-[3-(3-hydroxypropoxy)prop-1-en-1-yl]benzo[1,4]dioxine can be Prepared as Follows Following the procedure described in example 7§D, but starting from a mixture of trans-2,3-dihydro-6-(3-bromoprop-1-en-1-yl)benzo[1,4]dioxine and 2,3-dihydro-6-(1-bromoallyl)benzo[1,4]dioxine (650 mg), 296 mg of potassium hydroxide (296 mg 85% wt) and 1,3-propanediol (298 μL) in dimethylsulfoxide (1.8 mL) gives 280 mg of trans-2,3-dihydro-6-[3-(3-hydroxypropoxy)prop-1-en-1-yl]benzo[1,4]dioxine as a yellow oil used without further purification.

Rf TLC (heptane/ethyl acetate 2/1)=0.16

D The Mixture of trans-2,3-dihydro-6-(3-bromoprop-1-en-1-yl)benzo[1,4]dioxine and 2,3-dihydro-6-(1-bromoallyl)benzo[1,4]dioxine can be Prepared as Follows To a solution of 2,3-dihydro-6-(1-hydroxyallyl)benzo[1,4]dioxine (540 mg) in pyridine (20 μL) and petroleum ether (2 mL) stirred at a temperature close to −5° C. is added a solution of phosphorus tribromide (0.11 mL) in petroleum ether (1 mL). The mixture is stirred for three hour and an half at room temperature, diluted with diethyl oxide, washed successively with water and a saturated aqueous solution of sodium hydrogenocarbonate, dried over magnesium sulfate, filtered and concentrated to give 650 mg of a mixture of trans-2,3-dihydro-6-(3-bromoprop-1-en-1-yl)benzo[1,4]dioxine and 2,3-dihydro-6-(1-bromoallyl)benzo[1,4]dioxine as a yellow oil used without further purification.

E

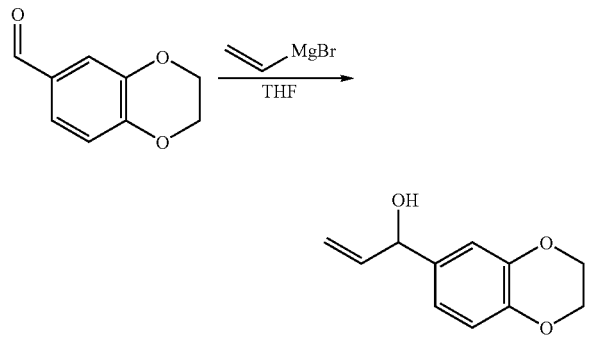

2,3-dihydro-6-(1-hydroxyallyl)benzo[1,4]dioxine can be Prepared as Follows

To a solution of vinylmagnesiumbromide in tetrahydrofurane (29 mL 1M) maintained at a temperature below 4° C. is added portionwise 2,3-dihydrobenzo[1,4]dioxine-6-carbaldehyde (4.32 g). The mixture is further stirred at a temperature close to 0° C. for 1.75 h and hydrolized by adding an aqueous solution of ammonium chloride (36.5 mL 1M). The mixture is extracted with diethyl oxide. The organic layers are pooled, washed with water, dried over magnesium sulfate, filtered and concentrated under reduced pressure. Purification by chromatography over silica gel, with heptane/ethyl acetate 1/1 as eluant, affords 1.12 g of 2,3-dihydro-6-(1-hydroxyallyl)benzo[1,4]dioxine as a yellow oil used without further purification.

Rf TLC (dichloromethane/methanol 95/5)=0.7

2,3-dihydrobenzo[1,4]dioxine-6-carbaldehyde can be obtained as described by S. Corsano et al., *Farmaco Ed. Sci.* 38(4) 265-73 (1983).

EXAMPLE 14

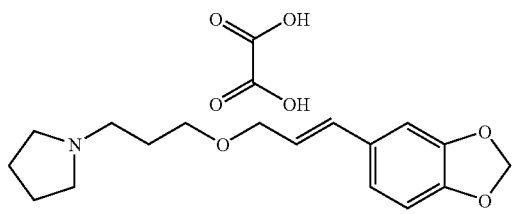

trans-1-{3-[3-(benzodioxol-5-yl)allyloxy]propyl}pyrrolidine, oxalate

Following the procedure described in example 2, but starting from trans-5-(3-hydroxyprop-1-en-1-yl)benzodioxolane (400 mg), potassium hydroxide (283 mg, 85% wt) and 1-(3-chloropropyl)pyrrolidine, hydrochloride (376 mg) in dimethylsufoxide (5 mL) affords 90 mg of trans-1-{3-[3-(benzodioxol-5-yl)allyloxy]-propyl}pyrrolidine, oxalate as a white solid melting at 109-111° C.

$^1$H NMR oxalate (DMSO)
7.09 (s, 1H, arom), 6.84 (m, 2H, arom), 6.49 (d, J=15.9 Hz, 1H, ArCH═), 6.18 (dt, J=15.9 Hz, J=5.9 Hz, 1H, CH═), 5.98 (s, 2H, OCH$_2$O), 4.02 (d, J=5.9 Hz, 2H, OCH$_2$), 3.44 (t, J=5.9 Hz, 2H, OCH$_2$), 3.13 (m, 6H, 3 CH$_2$N), 1.83 (m, 6H, 3 CH$_2$)

trans-5-(3-hydroxyprop-1-en-1-yl)benzodioxolane can be prepared as described by H.-L. Pan et al Synthesis 10 813-4 (1980) or W. E. Campbell, P. George *Phytochemistry* 21(6) 1455-6 (1982).

EXAMPLE 15

H$_3$ Binding

Membranes expressing human histamine H3 receptors were incubated 1 hour at room temperature in binding buffer containing 50 mM Na$_2$HPO$_4$/KH$_2$PO$_4$ pH 7.5 in a final volume of 200 μl. For binding experiments [$^{125}$]iodoproxyfan (2000 Ci/mmol; Amersham Pharmacia Biotech) concentrations ranged between 20 and 40 pM. Non-specific binding was determined in the presence of 1 μM Imetit. The reaction was stopped by rapid filtration through GF/B filters (pre-soaked for 2 hours with 0.3% polyethyleneimine) followed by 3 ice cold binding buffer washes. The filter-bound radioactivity was measured in a liquid scintillation counter with 50 μl of scintillation fluid.

The hH$_3$ binding investigated by use of [$^{125}$]iodoproxyfan gives a Kd=78±6 pM.

Representative results for the compounds of the invention are given below:

| Example nb° | Ki (nM) |
|---|---|
| 9 | 1.7 |
| 11 | 0.38 |
| 14 | 4.7 |

EXAMPLE 16

Cytochrome Inhibition

Cytochromes P-450 (CYPs) comprise a superfamily of hemoproteins that play an important role in the metabolism of a wide variety of xenobiotics and endogenous compounds. Among the xenobiotic-metabolizing CYPs, five forms, CYP1A2, CYP2C9, CYP2C19, CYP2D6 and CYP3A4 appear to be the major CYP isoforms responsible for the oxidative metabolism of drugs or xenobiotics. Inhibition of CYP-mediated metabolism, often the mechanism for drug-drug interactions, can limit the use of a drug because of adverse clinical effects. The potential for CYP enzyme inhibition is routinely assessed by performing in vitro inhibition studies by measuring the rates of metabolism of a probe biotransformation in the presence and absence of test molecules.

The ability of drug in human to inhibit the catalytic activity of cytochrome P-450 isoforms was assayed using microtiter plate-based, fluorometric assays for the activities of the five human major CYP forms. Inhibition potential was determined in vitro after incubation of fluorescent model substrates over various incubation time with human recombinant cytochrome isoforms in the absence or in presence of increasing concentrations of test molecules (from 1 nM to 100 μM), in comparison with specific CYP isoform inhibitors. Data were expressed as quantitative inhibition parameters [inhibitor concentration that produces 50% inhibition ($IC_{50}$ value)].

Incubation of drug was carried out at 37° C.±0.5° C. under agitation in the presence of human recombinant cytochrome P-450 isoforms and a NADPH generating system. The incubation conditions for each cytochrome isoform were as follow:

Representative cytochrome inhibition (IC50, concentrations for 50% inhibition) for the compounds of the invention are given below:

| Example nb | CYP3A4 | CYP2D6 |
|---|---|---|
| 1 | >10 μM | >10 μM |
| 2 | >10 μM | >10 μM |
| 3 | >10 μM | >10 μM |
| 4 | >10 μM | >10 μM |
| 5 | >10 μM | >1 μM |
| 6 | >10 μM | >1 μM |
| 7 | >100 μM | 81 μM |
| 8 | >10 μM | >1 μM |
| 9 | >100 μM | >100 μM |
| 10 | >10 μM | >1 μM |
| 11 | 23 μM | 18 μM |
| 12 | >10 μM | >1 μM |
| 13 | >10 μM | >10 μM |
| 14 | 10.6 μM | 4.4 μM |

EXAMPLE 17

COMPARATIVE EXAMPLE

Activity and cytochrome inhibition (IC50, concentrations for 50% inhibition) for compounds disclosed in WO 00/06254 are given below:

| | Cytochrome P-450 Enzyme | | | | |
|---|---|---|---|---|---|
| | CYP1A2 | CYP2C9 | CYP2C19 | CYP2D6 | CYP3A4 |
| NADPH Regenerating System | | | | | |
| NADP+ | 1.3 mM | 1.3 mM | 1.3 mM | 8.2 μM | 1.3 mM |
| Glucose-6-Phosphate | 3.3 mM | 3.3 mM | 3.3 mM | 0.41 mM | 3.3 mM |
| Magnesium Chloride Hexahydrate | 3.3 mM | 3.3 mM | 3.3 mM | 0.41 mM | 3.3 mM |
| Glucose-6-Phosphate Dehydrogenase | 0.4 Units/mL | 0.4 Units/mL | 0.4 Units/mL | 0.4 Units/mL | 0.4 Units/mL |
| Other Reagents | | | | | |
| $KPO_4$ buffer pH 7.4 | 100 mM | 25 mM | 50 mM | 100 mM | 200 mM |
| Positive Control (highest concentration) | Furafylline 100 μM | Sulfaphenazole 10 μM | Nootkatone 100 μM | Quinidine 10 μM | Ketoconazole 10 μM |
| Substrate | CEC 5 μM | MFC 75 μM | O-MF 2 μM | AMMC 1.5 μM | BFC 50 μM |
| Enzyme: recombinant CYP | 0.5 pmol | 1.0 pmol | 1.0 pmol | 1.5 pmol | 1.0 pmol |

CEC: 7-ethoxy-3-cyanocoumarin
MFC: 7-Methoxy-4-(trifluoromethyl)-coumarin
O-MF: 3-O-methyl fluorescein
AMMC: 3-[2-(N,N-diethyl-N-methylamino)ethyl]-7-methoxy-4-methylcoumarin
BFC: 7-Benzyloxy-4-(trifluoromethyl)-coumarin

| Example nb | | Ki (nm) | CYP2D6 |
|---|---|---|---|
| 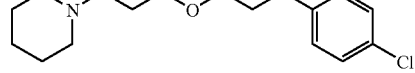 117 | | 2.4 | 0.059 μM |

It is apparent that the compounds of the invention surprisingly exhibit a significantly reduced cytochrome inhibition.

The invention claimed is:

1. A compound of formula (I):

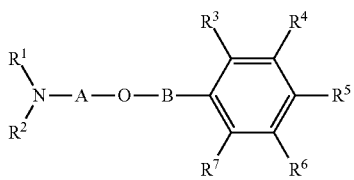

with $R^1$ and $R^2$ taken together with the nitrogen atom to which they are attached, form a saturated nitrogen-containing pyrrolidine ring:

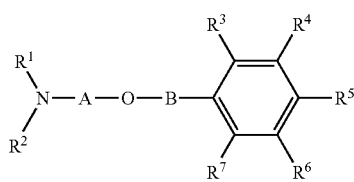

m being 4, each $R^a$, $R^b$ is independently identical or different, and $R^a$ represent a hydrogen and $R^b$ represents a hydrogen or a $C_1$-$C_4$ alkyl, wherein A is a saturated linear C2-C4 alkylene;

chain B is chosen from the groups selected within $C_3$-$C_4$ linear alkylene or $C_3$-$C_4$ linear alkenylene;

$R^5$ is chosen from a fluor atom, —O($C_1$-$C_4$)Alkyl, and each of $R^3$, $R^4$, $R^6$, $R^7$ represents H, or $R^4$ and $R^5$ form together a saturated heterocycle fused with the phenyl group, and each of $R^3$, $R^6$, $R^7$ represents H;

or their pharmaceutically acceptable salts, or their optical isomers, racemates, diastereomers or enantiomers.

2. Compound according to claim 1, wherein chain B is chosen from the groups selected within $C_3$-$C_4$ linear alkylene.

3. Compound according to claim 1, wherein each of $R_3$, $R_4$, $R_6$, $R_7$ represents H.

4. A compound of formula (I):

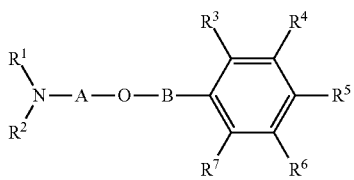

with $R^1$ and $R^2$ taken together with the nitrogen atom to which they are attached, form a saturated nitrogen-containing pyrrolidine ring:

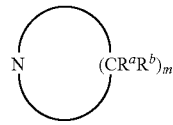

m being 4, each $R^a$, $R^b$ is independently identical or different, and $R^a$ represent a hydrogen and $R^b$ represents a hydrogen or a $C_1$-$C_4$ alkyl, wherein chain A is a saturated C1-C4 linear alkylene, chain B is chosen from the groups selected within $C_3$-$C_4$ linear alkylene or $C_3$-$C_4$ linear alkenylene;

$R^5$ is chosen from a fluor atom, and each of $R^3$, $R^4$, $R^6$, $R^7$ represents H, or $R^4$ and $R^5$ form together a saturated heterocycle fused with the phenyl group, and each of $R^3$ $R^6$, $R^7$ represents H;

or their pharmaceutically acceptable salts, or their optical isomers, racemates, diastereomers or enantiomers.

5. A compound of formula (I):

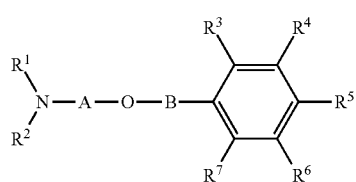

with $R^1$ and $R^2$ taken together with the nitrogen atom to which they are attached, form a saturated nitrogen-containing pyrrolidine ring:

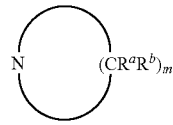

m being 4, each $R^a$, $R^b$ is independently identical or different, and $R^a$ represent a hydrogen and $R^b$ represents a hydrogen or a $C_1$-$C_4$ alkyl, chain A is a saturated C1-C4 linear alkylene, chain B is chosen from the groups selected within $C_3$-$C_4$ linear alkylene or $C_3$-$C_4$ linear alkenylene and $R^5$ is chosen from a fluor atom, —$C_1$-$C_4$ alkyl, —O($C_1$-$C_4$) Alkyl, —OH, $CF_3$, an unbranched or branched alkenyl, an unbranched or branched alkynyl, —O(aryl), —$CH_2CN$, —(O)$_n$—X—$NR^8R^9$ wherein n=0 or 1, X represents an alkylene, alkenylene, alkynylene, with $R^8$ and $R^9$ representing independently hydrogen, a straight or branched $C_1$-$C_4$ alkyl, an aryl group or taken together with the nitrogen atom to which they are attached form a saturated or partially unsaturated monocyclic or bicyclic heterocycle;

or $R^4$ and $R^5$ form together a cycle or heterocycle, fused with the phenyl group, said cycle or heterocycle being aromatic, saturated, unsaturated or partially unsaturated, each of $R^3$, $R^4$, $R^6$, $R^7$ identical or different independently represents a group chosen from H, —$C_1$-$C_4$ alkyl, halogen atom, —O($C_1$-$C_4$)Alkyl, —OH, $CF_3$, an unbranched or branched alkene, an unbranched or branched alkyne, —O(aryl), —$CH_2CN$, —(O)$_n$—X—$NR^8R^9$ wherein n=0 or 1, X represents an alkylene, alkenylene, alkynylene, with $R^8$ and $R^9$ representing independently hydrogen, a straight or branched $C_1$-$C_4$ alkyl, an aryl group or taken together with the nitrogen atom to which they are attached form a saturated or partially unsaturated monocyclic or bicyclic heterocycle;

or $R^3$ and $R^4$ form together a cycle or heterocycle, fused with the phenyl group, said cycle or heterocycle being aromatic, saturated, unsaturated or partially unsaturated, or their pharmaceutically acceptable salts, or their optical isomers, racemates, diastereomers or enantiomers.

chosen from:
1{3-[(3,4-dimethoxyphenyl)propoxy]propyl}pyrrolidine,
1{3-[3-(4-fluorophenyl)propoxy]propyl}pyrrolidine,
trans-1-{3-[3(4-fluoro-3-methoxyphenyl)allyloxy] propyl}pyrrolidine,
1-{3-[3-(4-fluoro-3-methoxyphenyl)propoxy] propyl}pyrrolidine,
1-{3-[3-(4-fluoro-3-methylphenyl)propoxy] propyl}pyrrolidine,
1-{3-[3-(4-fluoro-2-methoxyphenyl)propoxy] propyl}pyrrolidine,
trans-1-{3-[3-(benzofuran-5-yl)allyloxy] propyl}pyrrolidine,
trans-1-{3-[3-(benzodioxol-5-yl)allyloxy] propyl}pyrrolidine, or their pharmaceutically acceptable salts, or their optical isomers, racemates, diastereomers or enantiomers.

6. Compound according to claim 5 which is 1-{3-[3-(4-fluorophenyl)propoxy]propyl}pyrrolidine,
or its pharmaceutically acceptable salts, or its optical isomers, racemates, diastereomers or enantiomers.

7. Compounds according to claim 5 chosen from:
1-{3-[3-(3,4-dimethoxyphenyl)propoxy] propyl}pyrrolidine,
1-{3-[3-(4-fluorophenyl)propoxy]propyl}pyrrolidine,
1-{3-[3-(4-fluoro-3-methoxyphenyl)propoxy] propyl}pyrrolidine,
trans-1-{3[3-(benzodioxol-5yl)allyloxy] propyl}pyrrolidine, or their pharmaceutically acceptable salts, or their optical isomers, racemates, diastereomers or enantiomers.

8. Compounds according to claim 5 chosen from:
1-{3-[3-(4-fluorophenyl)propoxy]propyl}pyrrolidine,
trans-1-{3-[3-(benzodioxol-5-yl)allyloxy] propyl}pyrrolidine, or their pharmaceutically acceptable salts, or their optical isomers, racemates, diastereomers or enantiomers.

9. Process of preparation of a compound according to claim 1 comprising the step of reacting a corresponding compound of formula (II)

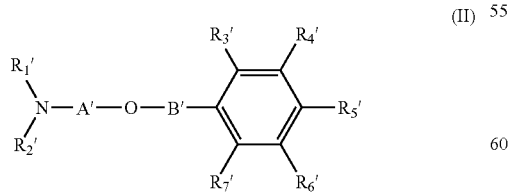

(II)

wherein A', B', $R_1'$, $R_2'$, $R_3'$, $R_4'$, $R_5'$, $R_6'$ and $R_7'$ represent respectively A, B, $R_1$, $R_2$, $R_3$, $R_4$, $R_5$, $R_6$ and $R_7$ or a precursor group of respectively A, B, $R_1$, $R_2$, $R_3$, $R_4$, $R_5$, $R_6$ and $R_7$ with a suitable reagent.

10. Process of preparation of a compound of formula (I) according to claim 1 comprising the step of reacting corresponding compounds of formula (III) and (IV):

(III)

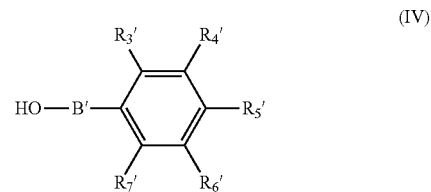

(IV)

in which wherein A', B', $R_1'$, $R_2'$, $R_3'$, $R_4'$, $R_5'$, $R_6'$ and $R_7'$ represent respectively A, B, $R_1$, $R_2$, $R_3$, $R_4$, $R_5$, $R_6$ and $R_7$ or a precursor group of respectively A, B, $R_1$, $R_2$, $R_3$, $R_4$, $R_5$, $R_6$ and $R_7$ and X represents a halogen atom.

11. Process of preparation of a compound of formula (I) according to claim 1 comprising the step of reacting corresponding compounds of formula (V) and (VI):

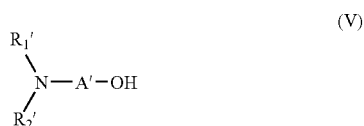

(V)

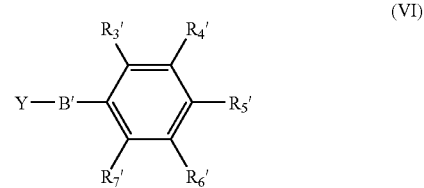

(VI)

in which wherein A', B', $R_1'$, $R_2'$, $R_3'$, $R_4'$, $R_5'$, $R_6'$ and $R_7'$ represent respectively A, B, $R_1$, $R_2$, $R_3$, $R_4$, $R_5$, $R_6$ and $R_7$ or a precursor group of respectively A, B, $R_1$, $R_2$, $R_3$, $R_4$, $R_5$, $R_6$ and $R_7$ and Y represents a leaving group.

12. Process of preparation of a compound of formula (I) according to claim 1 comprising the step of reacting corresponding compounds of formula (VII) and (VIII):

(VII)

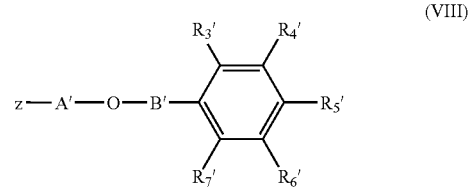

(VIII)

in which wherein A', B', $R_2'$, $R_3'$, $R_4'$, $R_5'$, $R_6'$ and $R_7'$ represent respectively A, B, $R_1$, $R_2$, $R_3$, $R_4$, $R_5$, $R_6$ and $R_7$ or a precursor group of respectively A, B, $R_1$, $R_2$, $R_3$, $R_4$, $R_5$, $R_6$ and $R_7$ and Z represents a halogen atom.

13. A pharmaceutical composition comprising a compound of formula (I) according to claim 1 with a pharmaceutically acceptable excipient or carrier.

* * * * *